(12) United States Patent
Bickar

(10) Patent No.: US 6,338,967 B1
(45) Date of Patent: Jan. 15, 2002

(54) SOLID SOLVENTLESS PROTEIN ASSAY WITH STANDARDS

(76) Inventor: David Bickar, 27 Stone Path La., Easthampton, MA (US) 01027

( * ) Notice: Subject to any disclaimer, the term of this patent is extended or adjusted under 35 U.S.C. 154(b) by 0 days.

(21) Appl. No.: 09/351,117

(22) Filed: Jul. 10, 1999

Related U.S. Application Data (60) Provisional application No. 60/092,456, filed on Jul. 11, 1998.

(51) Int. Cl.⁷ .............................................. G01N 33/00
(52) U.S. Cl. ............................... 436/86; 436/8; 436/15
(58) Field of Search ............................... 436/8, 15, 18, 436/86, 87, 88

(56) References Cited

U.S. PATENT DOCUMENTS

| | | | |
|---|---|---|---|
| 3,898,172 A | 8/1975 | Reif et al. | 252/408.1 |
| 4,023,933 A | 5/1977 | Bradford et al. | 436/87 |
| 4,219,337 A | 8/1980 | Grossberg et al. | 436/86 |
| 4,305,721 A | 12/1981 | Bernstein | 436/518 |
| 4,337,064 A | 6/1982 | Gindler | 436/88 |
| 4,507,233 A | 3/1985 | Saito et al. | 530/363 |
| 4,859,421 A | 8/1989 | Apicella | 422/61 |
| 5,073,341 A | 12/1991 | Hargreaves | 422/58 |
| 5,077,222 A | 12/1991 | Lau | 436/88 |
| 5,132,085 A | 7/1992 | Pelanek | 422/55 |
| 5,908,787 A | * 6/1999 | Cast et al. | 436/86 |

FOREIGN PATENT DOCUMENTS

CA    2132413    3/1995

OTHER PUBLICATIONS

Read & Northcote, Anal. Biochem. 116:53–64 (1981).
Compton & Jones, Anal. Biochem. 151:369–374 (1985).

* cited by examiner

Primary Examiner—Maureen M. Wallenhorst
(74) Attorney, Agent, or Firm—Paul G. Lunn, Esp.

(57) ABSTRACT

Reagent composition and quantities used to prepare a simple, solid stable and reproducible protein assay and reproducible solventless protein assay standard. The method of preparing the protein assay and protein assay standards is also described. A solidifying agent such as a solid acid is added to the dye reagent solution prior to removal of solvent so as to produce a solid dye assay reagent.

18 Claims, 2 Drawing Sheets

SOLID SOLVENTLESS PROTEIN ASSAY WITH STANDARDS

The present application claims the benefit of U.S. Provisional Application No. 60/092,456 filed Jul. 11, 1998.

FIELD OF THE INVENTION

The present invention lies in the field of protein chemistry.

BACKGROUND OF THE INVENTION

The determination of the total protein present within a solution is important in many analytical procedures such as in the determination of the purity of a protein and in determining the protein chemistry of a blood or urine sample. Four spectroscopic methods are routinely used to make such determinations. These include measurement of the protein's intrinsic ultraviolet (U.V.) absorbance, and three methods which generate a protein-dependent color change, namely, the Lowry assay, the Smith copper/bicinchoninic assay, and the Bradford dye assay, U.S. Pat. No. 4,023,933. Although one or more of these methods is used routinely in almost every biochemical laboratory, none of these procedures are particularly convenient for the following reasons.

The first, U.V. absorbance, has limited application because it requires a pure protein with know extinction coefficient in a solution free of interfering substances. The Lowry and copper/bicinchoninic assays require the preparation of several reagent solutions which must be carefully measured and mixed during the assay. This is followed by lengthy, precisely timed incubations at closely controlled elevated temperatures, then immediate absorbance measurements of the unstable solutions. Both assays may be affected by other substances frequently present in biochemical solutions, including detergents, lipids, buffers and reducing agents. To control for these factors each assay must also include a series of standards, each with a different, known concentration of added protein but otherwise having the same composition as the sample solutions. The Bradford dye assay is faster, involves fewer mixing steps, does not require heating, and gives a more stable calorimetric response than the two previous assays. Like them, however, its response is prone to influence from nonprotein sources and protein standard solutions must be used.

The preparation of protein standards is tedious and error-prone. Protein preparations, often of bovine serum albumin, are available as preweighed powder or in sterile solutions of measured concentration, but their use in preparing standard solutions still requires several precise measurements and dilutions. Frequently this involves compromises between convenience, precision, and the requirement that the standards contain the same concentrations of non-protein components as the sample solutions.

U.S. Pat. No. 5,496,737 (hereinafter the '737 patent) discloses a process for producing a solventless protein assay standard, which largely solved the problems of the prior art. This patent teaches a method for preparing convenient and stable protein assays and protein assays with included standards. Even though the process of the '737 patent solved many of the problems associated with previous protein assays, the process and the resultant preparations still had a number of problems which made the process and product not quite suitable for mass production and commercial use. The most serious of these is that the primary buffer component of the anhydrous dye reagent mixture used in the solventless protein assay is phosphoric acid. This causes the dye reagent mixture to have the properties of a viscous liquid upon drying. Because of this, if the plate is inverted during storage or shipping, the anhydrous reagent mixture may slowly flow out of the receptacle or onto the cap or tape seal. This could cause the dye reagent to be lost when the cap or tape was removed, and thereby decrease the colorimetric response of the assay. It also makes it difficult to prevent any added protein standards from mixing with the dye reagent. Although this is normally not a problem, as the anhydrous protein shows little or no reaction with the anhydrous dye reagent, in the presence of water the acidic dye reagent catalyzes protein hydrolysis. Because the dye does not bind to the small peptides or individual amino acids produced by protein hydrolysis, if water or water vapor were allowed to enter the receptacle before it was used in an assay, this could cause the colorimetric response to the protein to decrease when an assay was performed.

Thus, there is a need for a solventless dye reagent and a solventless protein assay preparation in which the buffering agent does not remain liquid, but is crystallized or forms a solid upon drying.

SUMMARY OF THE INVENTION

The present invention fills this need by providing for a dye assay reagent mixture comprised of a protein reacting dye and a solidifying agent such as a solid acid.

The present invention further provides for method for preparing a solventless dye assay reagent comprising preparing a dye solution containing a dye, a dye solvent and a solidifying agent; placing an aliquot of the dye solution within a receptacle; removing the dye solvent under conditions wherein the solidifying agent precipitates, crystallizes or solidifies. Preferred dyes are those listed in Table 1. A most preferred dye is Coomassie blue G250 (C.I. 42655). In a preferred embodiment, the solidifying agent is a solid acid. Preferred solid acids are those listed in Table 2. In even a more preferred method of the present invention a stabilizer is added such as those listed in Table 3.

The present invention further provides for a solventless protein assay standard comprised of a protein reacting dye and a solidifying agent such as a solid acid, and a solventless protein.

The present invention further provides for a method for preparing a solventless protein standard. The standard is prepared by preparing a dye solution containing a dye, a dye solvent and a solidifying agent, placing an aliquot of the dye solution within a receptacle, removing the dye solvent under conditions wherein the solidifying agent solidifies. A protein solution containing a known amount of protein and a known amount of protein solvent is prepared; a known amount of the protein solution is placed within the receptacle containing the dye such that the amount of protein within the receptacle can be calculated, and the protein solvent is removed. The preferred dyes are listed in Table 1; and the preferred dye is Coomassie blue G250 [Color Index (C.I. 42655]. Preferred solidifying agents are solid acids particularly, those listed in Table 2, particularly sodium bisulfate. In a preferred embodiment a stabilizer is added such as those in Table 3.

In an alternative process the order in which the dye reagent and protein are placed in the receptacle is reversed. In this embodiment, the solventless protein acid standard is prepared by preparing a protein solution containing a known amount of protein and a known amount of protein solvent. A known amount of the protein solution is placed within a receptacle such that the amount of protein within the receptacle can be calculated. The protein solvent is removed. A dye solution containing a dye, dye solvent and a dissolved solid acid is prepared. An aliquot of the dye solution is placed within the receptacle containing the protein the dye solvent removed under conditions wherein the solid acid precipitates, crystallizes or solidifies. The preferred dyes, solidifying agents and stabilizers are the same as listed above.

The present invention further provides for solventless, protein-assay standard comprised of a receptacle, said receptacle containing a solventless dye reagent with a solidifying agent and a dehydrated protein wherein upon addition of an appropriate solvent the dye reagent and protein react together to produce a detectable color indicating the presence and/or concentration of protein.

The present invention further provides for an apparatus comprised of a series of receptacles such as a multiwell or microtiter plate wherein one or more of the receptacles contain a known concentration of dehydrated protein, a protein-reactive reagent and a solidifying agent such that upon addition of an appropriate solvent, the reagent and protein react to indicate the presence and/or concentration of protein.

The present invention further provides for one or more of the receptacles contain only the dye and solidifying agent and one or more of the receptacles contain the dehydrated protein, the protein-reactive reagent and solidifying agent.

BRIEF DESCRIPTION OF THE FIGURES

FIG. 1 represents a multiwell plate like that used in Example 1. Each well initially contained the solventless dye, and solidifying agent, and the wells in columns 1,4, 7 and 10 also contained the anhydrous protein standards. The wells were treated with 100 $\mu$L of water to produce a protein concentration-dependent color change.

DETAILED DESCRIPTION OF THE INVENTION

The teachings of all of the references cited herein are incorporated in their entirety herein by reference.

Definitions

"Solid" and "solidify"—"Solid" and "solidify" are used in the conventional sense, and so include the sense of the state and/or formation of a precipitate, crystal, polymer and co-crystalled material, and also to include any state and/or formation of a semi-solid mass.

"Solidifying agent"—is a chemical substance which when in solution can be combined with the dye solution, and which when the solvent is removed causes the reagents to solidify. The solidifying agent must be a substance that does not interfere with a protein assay.

"Solid acid"—A "solid acid" is a chemical substance or mixture of substances which while at or near room temperature (25° C.) has a solid or semi-solid consistency in the anhydrous or minimally-hydrated state. Examples of solid acids are shown in Table 2. A solid acid such as, for example, a mixture of sodium bisulfate ($NaHSO_4$) and sulfuric acid ($H_2SO_4$), forms a crystalline solid upon drying that adheres firmly to the bottom of the well. An additional advantage provided by this mixture is that both sodium bisulfate and sulfuric acid dissolve readily with added water and these compounds are stronger acids than phosphoric acid, so less of the sodium bisulfate-sulfuric acid mixture is required to produce the acidic conditions required for the a protein assay using Coomassie blue G250 C.I 42655.

Sulfuric acid can be used to acidify the assay medium, as long as its concentration is such that the pH of the assay medium is maintained in the range to provide the maxim dye response upon protein binding (around pH 1.1). Using less acid also improves mixing since there is less dye reagent to dissolve. Additionally, because the anhydrous dye reagent forms a solid mass rather than a viscous liquid, protein standards can be more easily added to the receptacle and dried in such a way that they do not come in contact with the dye reagents. This prevents the risk of protein hydrolysis if, for example, the receptacle is opened briefly and the contents exposed to water vapor at sometime before the contents are used in an assay. Other acidic media are also possible. The necessary features include high (>1 M) solubility and rapid dissolution in aqueous solution, the ability to maintain a pH of 1.1, low volatility, a solid or semi-solid dry form, compatibility with the other components of the assay and the receptacle, and long-term stability.

"Stabilizer"—A "stabilizer" is any substance which helps to stabilize the protein standards or protein-dye complex, either prior to or during the course of a protein assay. The stabilizer is added to help to stabilize the protein standards in the presence of the dried assay reagents, and to stabilize the colorimetric protein-dye reaction products and prevent their precipitation. It also acts to reduce the surface tension of the assay solution and thereby destabilize any bubbles produced by too-vigorous shaking. The additional features of a stabilizer are that it should not interfere with preparation or storage of the assay preparations, and so must be unreactive with the assay medium or receptacle, and it must be relatively nonvolatile, and so not lost during preparation or storage. Ideally, it should also improve the assay sensitivity and stability. Several compounds or admixtures of compounds having some or all of these desirable qualities are shown in Table 3. Derivatives of either ethylene glycol or of propylene glycol appear to be some of the most useful of these compounds, with triethylene glycol and 2-(2-methoxyethoxy)ethanol being notable examples. At the right concentrations, these compounds were found to greatly reduce or eliminate the precipitation of the protein-dye complex, and hence to increase the time during which sample readings could be obtained. They also decreased the surface tension of the assay solutions, and so decreased the stability of any bubbles formed during mixing, thereby reducing a possible cause of inaccurate absorbance readings. The stabilizers should be added to the dye solution, acid solution or to the combined solutions of acid preferably at a concentration 8–10% volume/volume.

"Color" and "light absorbance"—According to the present invention, "color" and "light absorbance" are defined as any change in the frequency, intensity or spectral envelope of the light absorbance, emission or fluorescence that occurs due to the reaction of the protein-reactive reagent with a protein.

Thus the present invention, as stated above, is directed to a method for preparing a solventless dye assay reagent comprising preparing a dye reagent solution containing a dye, a dye solvent and a solidifying agent; placing an aliquot of the dye reagent solution within a receptacle; removing the dye solvent under conditions wherein the solidifying agent precipitates.

An additional embodiment relates to a solventless dye reagent produced according to the above-described process.

Another embodiment of the present invention is directed toward a method for preparing a solventless protein standard comprising the steps of: preparing a dye solution containing a dye, a dye solvent and a solidifying agent; placing an aliquot of the dye solution within a receptacle; removing the dye solvent under conditions wherein the solidifying agent solidifies. A protein solution is then prepared containing a known amount of protein and a known amount of protein solvent. A known amount of the protein solution is placed within the receptacle containing the dye such that the amount of protein within the receptacle can be calculated. The protein solvent is then removed.

In a preferred embodiment, the solventless dye assay reagent is placed in a number wells in a multiwell plate. A number of separate protein solutions are prepared, and each protein solution has a different known amount of protein and a known amount of protein solvent, wherein the concentration of protein within each protein solution is known and is different than the concentration of the other solutions. A known amount of each of the protein solutions is then placed into separate dye assay reagent-containing wells of the multiwell plate. The protein solvent is then removed from wells containing a protein solution.

In another embodiment the present invention is directed towards a method for determining the concentration of total protein in a solution. A dye reagent solution is prepared containing a dye, a dye solvent and a solidifying agent. An aliquot of the dye reagent solution is placed into each of a series of wells within a multiwell plate. The dye solvent is removed under conditions wherein the solidifying agent precipitates, cyrstallizes or solidifies. A number of separate protein solutions are prepared, each protein solution containing a different known amount of protein and a known amount of protein solvent, wherein the concentration of protein within each protein solution is known and is different than the concentration of the other solutions. A known amount of each of the protein solutions is placed into separate dye reagent containing wells such that the amount of protein within each well is different. The protein solvent is removed from the protein containing wells. A predetermined uniform volume of solvent is added to each of the wells which contain protein so as to produce a detectable visual protein-dye reaction. The visual protein-dye reaction in each of the well has an intensity which corresponds to the concentration of protein within each of the wells. A volume of a protein solution having an unknown concentration of protein is added to a well which only contains a solventless dye reagent and no protein. The volume of unknown protein solution is in an amount equal to the volume of solvent added to the protein-dye containing wells, wherein the protein in the unknown solution reacts with the dye in the well to produce a detectable visual protein-dye reaction which has a measurable intensity. The intensity of the protein-dye reaction within the well containing the protein solution having an unknown concentration of protein is compared with the intensities of the protein-dye reactions of the wells containing known amounts of protein which indicates the concentration of protein within the unknown protein solution. See FIG. 2.

As was stated above, the present invention provides for a semi-solid or solid dye reagent and a semi-solid or solid protein assay standard. The is enables a solventless protein assay standard produced to be produced as a commercially viable product. Accordingly, the present invention is comprised of a receptacle, said receptacle containing a solventless reagent dye, a solidifying agent, stabilizer and a dehydrated protein, wherein upon addition of an appropriate solvent the reagent and protein react together to produce a detectable color change indicating the presence and/or amount of protein.

The present invention is further comprised of a method for preparing a solventless protein assay in which a dye and solidifying agent are included, and which may also include a predetermined amount of protein. An aliquot of the dye solution containing a solid acid in solution is placed into an appropriate receptacle such as the well of a multiwell plate and the solvent is removed from the dye solution resulting in solventless dye being within the receptacle. For the solventless protein assay standards, an aliquot of the protein solution is then placed within the same receptacle as the dye and on top of the dye. The solvent is removed from the protein solution in such a manner that the protein is not hydrolyzed. This results in an solventless protein standard in which the solventless protein, solventless dye and solid acid are contained within the same receptacle. When an appropriate solvent is added to the receptacle, the protein and dye react together to produce a detectable color change.

Furthermore, to determine the concentration of protein in a solution, the solventless protein-reactive dye can be placed into a receptacle, but without the addition of protein. A volume of the solution (corresponding to the volume of the solvent placed into the receptacles with the known protein/dye mixture above) containing an unknown amount of protein can be placed into the receptacle containing only the protein-reactive reagent. The resultant color of the solution of unknown is then compared to the color of each of the solutions containing known amounts of protein. The concentration of protein in the solution of unknown will approximate the protein concentration of the known solution whose color is closest to the color of the unknown solution. See FIG. 2

More accurate estimations of protein concentration can be made spectrophotometrically determining the light absorbance for each of the receptacles in a series of protein/reagent mixtures. By plotting the light absorbance of the solutions against the concentration of protein contained in each of the receptacles in the series, a line showing the light absorbance for any concentration of protein up to that of the highest in the series can be made. By then measuring the light absorbance of a solution containing an unknown concentration of protein, the concentration of protein in the solution can be determined from the graph, by finding the protein concentration at which the absorbance value for the line is equal to the absorbance of the solution.

According to the present invention, to measure the concentration of a protein, the dye and protein must react in solution under conditions wherein protein binding causes the dye to undergo a color change due to a change in its protonation state. For this to occur, the pH of the protein/dye solution must near the pKa of the ionizable group of the dye responsible for the color change.

Figure 1:
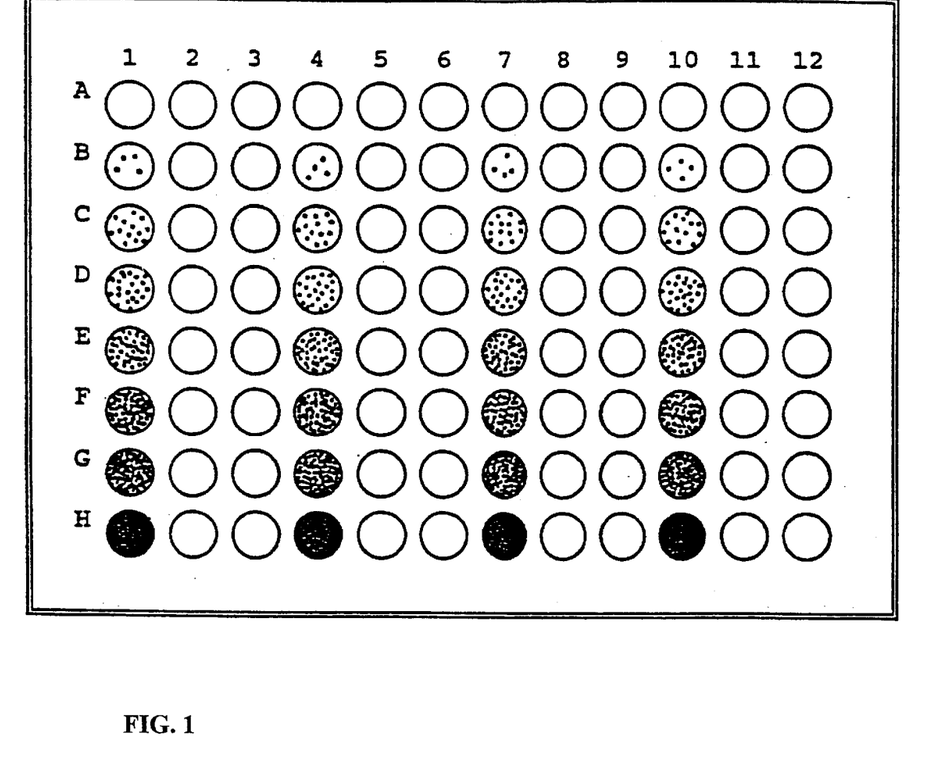
Figure 2:
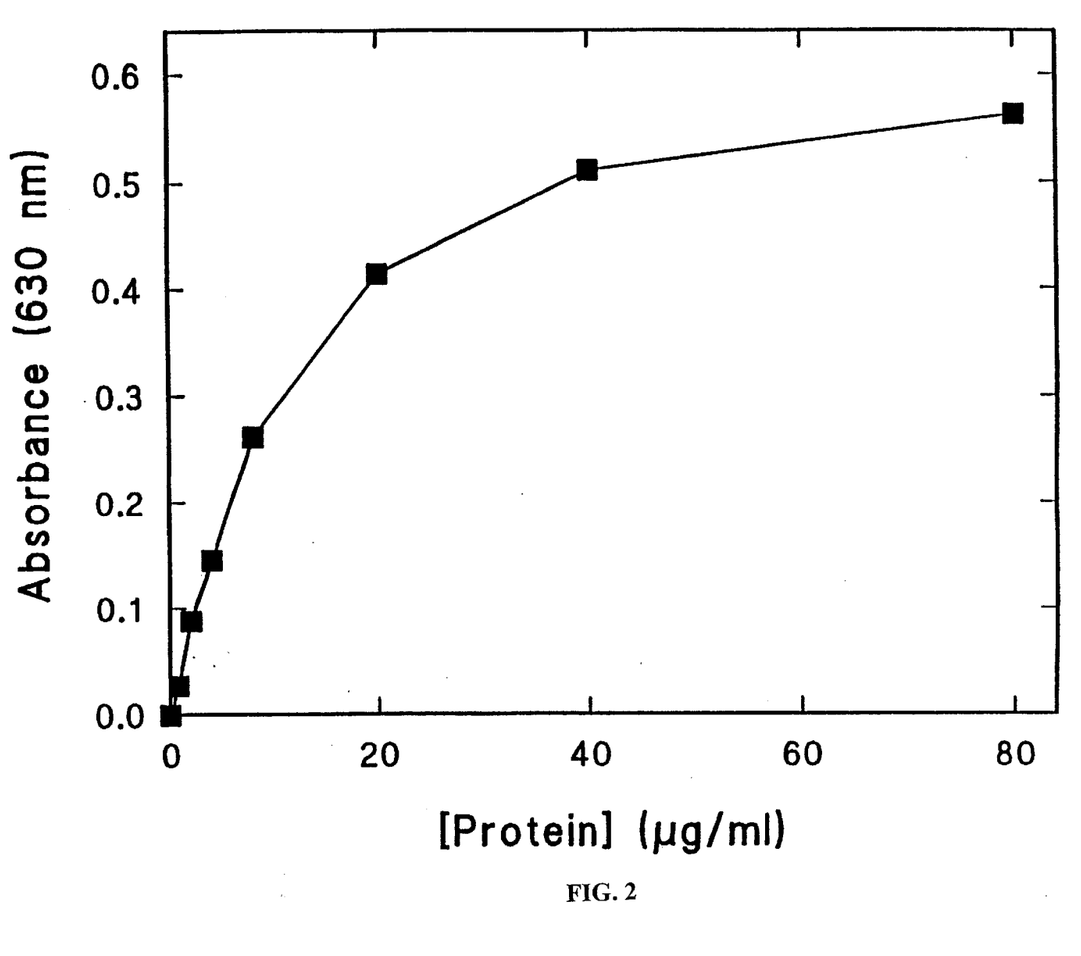
FIG. 2 shows a graph of Absorbance (630 nm) vs. [Protein] ($\mu$g/mL) for a multiwell plate with solventless dye and anhydrous protein standards prepared as described in the examples. To each well was added 100 $\mu$L of distilled water per well and their absorbance at 600 nm determined.

FIGS. 1 and 2 illustrate a preferred embodiment of the present invention. FIG. 1 is a multiwell plate having 96 wells. A dye solution is prepared for example, Coomassie blue G250(CI. 42655) dissolved in methanol, is prepared. The pH of the dye solution must then be adjusted by a buffer. In order to optimize the colorimetric response upon dye-protein binding, the pH of the solution should be between pH 0.5 and 3.0, and preferably around pH 1.1. In the prior art Bradford assay the buffer was generally phosphoric which remained a liquid when the solvent was removed from the dye in the process of '737 patent. However, according to the present invention, the buffer is prepared by dissolving a solid acid, for example sodium bisulfate dissolved in an aqueous solution contain sulfuric acid as described in Example 1. Aliquots of the dye and buffer solution are added to each of the wells of all of the rows of FIG. 1. The dye reagent mixture is then dried. A solid acid such as sodium bisulfate not only contributes to bringing the dye solution to a proper pH, but when it is dried it crystallizes or solidifies and thus the problem of the prior art '737 is solved. The dye reagent is no longer a viscous liquid but is a solid and thus can be shipped commercially.

After the dye reagent solution is dried a series of protein solutions is prepared, each protein solution having a different concentration of protein. Aliquots of the protein solutions are then placed on top of the dried dye reagent in the wells of rows 1, 4, 7, and 10. In Example 1 the concentration of the protein solutions were as follows:

1000 μg/mL in the wells 1H, 4H, 7H and 10H;
500 μg/mL in the wells 1G, 4G, 7G and 10G;
200 μg/mL in the wells 1F, 4F, 7F and 10F;
100 μg/mL in the wells 1E, 4E, 7E and 10E;
50 μg/mL in the wells 1D, 4D, 7D and 10D;
20 μg/mL in the wells 1C, 4C, 7C and 10C;
10 μg/mL in the wells 1B, 4B, 7B and 10B; and
0 μg/mL in the wells 1B, 4B, 7B and 10A.

The solvent, generally water, is then removed from the protein solution resulting in a solventless protein assay standard which is solid and commercially viable. Into the wells of rows 2, 3, 5, 6, 8, 9, 11 and 12, which only contain solventless solid dye reagent, can be placed aliquots of protein solution in which the concentration of the protein is unknown. Aliquots of solvent equal to the volume of the unknown solution, which was added to the dye reagent containing well, can then be added to the wells in rows 1, 4, 7 and 10. The color change brought about by the dye protein reactions can be compared between the known versus the unknown protein solutions and thus the concentration of the unknown protein solution determined.

I. Dye Reagent Preparation

During the dye reagent preparation, a dye, buffering agent and solidifying agent, which preferably is a buffering agent, are placed in a receptacle, either as separate solutions or in combination, and their solvents removed. In the process or method of the present invention as defined in the claims, the phrase "preparing a dye solution containing a dye, a dye solvent and a solidifying agent; placing an aliquot of the dye reagent solution within a receptacle;" emcompasses both cases either where the dye and acid solutions are placed into the receptacle separately or are first mixed together and then placed into the receptacle. This is also the case when the solidifying agent is a solid acid, as for example, those listed in Table 2. In general, the solventless dye reagent of the present invention will be composed of a solventless dye, a buffering agent, a solidifying agent which may also act as the buffering agent during a protein assay. In addition, a stabilizer may be added to improve the stability of a protein/dye response. Furthermore, a solventless protein standard will have as its components the solventless dye reagent and a solventless protein. The individual steps of the process of the present invention are described in detail below.

A. Selection of Dye

Any dye which upon binding or reacting with a protein can undergo a change in spectroscopic properties can be used for protein determination. Some of the important properties of a dye for predicting its usefulness in protein determination include its affinity for different proteins, reactions with interfering substances, stability, solubility, absorbance maximum and extinction coefficient.

Preferred dyes include those listed below in Table 1.

TABLE 1

| Preferred Protein Dyes | |
|---|---|
| Acid Violet 17 | (C.I. 42650) |
| Coomassie blue G250 | (C.I. 42655) |
| Serva Blue W | (C.I. 42645) |
| Ponceau S | (C.I. 27195) |
| Fast Green FCF | (C.I. 42053) |
| Eosin Y | (C.I. 45380) |
| Reactive Blue 15 | (C.I. 61205) |
| Reactive Red 4 | (C.I. 18105) |
| Stains-All | (C.I. 62160) |
| Benzyl Violet | (C.I. 42640) |

B. Solvent Used with the Dye

The solvent used to dissolve the dye is dependent on the particular dye employed, and the final assay conditions required. In addition to aqueous and organic solvents and their mixtures, other useful solvents include organic and inorganic acids, such as acetic, phosphoric, polyphosphoric and sulfuric acids. Bases, such as pyridine and triethylamine may also be used.

C. Selection of Buffering Agent

The buffering agent must maintain the pH of the assay medium within the range near the pKa of the ionizable group of the dye responsible for the color change on protein binding. Depending on the pKa of the ionizable group of a particular dye, the buffering agent may act as an acid or a base relative to the pH of water. For example, when using Coomassie blue G250 (C.I. 42655), in order to optimize the calorimetric response upon dye-protein binding, the pH of the solution should be between pH 0.5 and 3.0, and preferably around pH 1.1.

D. Selection of the Solidifying Agent

The solidifying agent causes the dye reagent to solidify. The solidifying agent must be a substance that does not interfere with the reaction of the dye with the protein, and preferably is also a solid buffering agent. The amount of solidifying agent used must be sufficient to ensure solidification of the dye reagent. A solidifying agent that is also a buffering agent, a solid acid, might be used alone or in combination with other, liquid buffering agents to achieve the desired pH for the assay medium, and to optimize the rate of dissolution of the resultant dye reagent. To increase the rate of dissolution of the resultant assay preparation, a combination of solid and liquid acids can be used. A sufficient amount of solid acid should be used to ensure solidification of the solventless dye reagent, but small enough to allow rapid dissolution of the reagent upon addition of solvent. In a preferred embodiment the solidifying agent is a solid acid, especially those contained in Table 2. See examples 1 and 2 for examples using Coomassie blue G250 (C.I. 42655) with sodium bisulfate ($NaHSO_4$) and sulfuric acid ($H_2SO_4$).

E. Stabilizer

A stabilizer is added to help to stabilize the protein standards in the presence of the dried assay reagents. An effective stabilizer has properties, the most important being its ability to stabilize the colorimetric protein-dye reaction product while preventing its precipitation, and reducing the surface tension of the assay solution and thereby destabilize any bubbles produced by too-vigorous shaking. The additional requirements for the stabilizer are that it should not interfere with preparation or storage of the assay medium, and so must be unreactive with the assay medium or plastic plate, and it must be relatively nonvolatile, so it is not lost during preparation or storage. Additionally, it should improve the actual assay sensitivity and stability. Several compounds or admixtures of compounds, were found to have some or all of these desirable qualities. The most useful of these were derivatives of either ethylene glycol or of propylene glycol, with triethylene glycol and 2-(2-methoxyethoxy)ethanol being notable examples. At the right concentrations, these compounds were found to greatly reduce or eliminate the precipitation of the protein-dye complex, and hence to increase the time during which sample readings could be obtained. They also decreased the surface tension of the assay solutions, and so decreased the stability of any bubbles formed during mixing, thereby reducing a possible cause of inaccurate absorbance readings. See Table 3 for examples of proper stabilizers. The stabilizer, if added, should be added to the dye reagent solution to give a concentration of 8–10% (v/v).

F. Solvent Removal

Solvents can be removed by evaporation, aided by heating, reduced pressure, or a stream of gas or air. Care must be taken that the conditions used do not degrade or remove the dye or other reagents necessary for the assay.

II. Placing the Dye on the Multiwell Plate

A. Dye Addition

A dye in solution, as well as other reagents necessary for the protein assay, can be easily and accurately added to the wells of a multiwell plate. Small volumes of solutions containing accurately measured amounts of the necessary reagents can be added to each well using standard laboratory equipment, including automated devices for multiple additions. Preferred dyes are those shown in Table I. The buffering solution and dye solution can be mixed together and then added to a receptacle or added separately to a receptacle.

III. Preparation of Protein Standards

A. Protein Used

The protein used to prepare the standards should give a response on reaction with the chosen dye sufficient to allow the concentration of protein in a solution to be determined by comparing the dye response of the solution of unknown protein concentration with the dye responses of protein standard solutions. A typical protein is a serum albumin such as bovine serum albumin (BSA).

B. Solvent Used for Protein Standards

Protein standards should be prepared in solvents which provide sufficient solubility and protein stability to ensure reproducible applications. The solvent should also be easily removed, and not interfere with the subsequent assay. Detergents or buffer concentrations which interfere with the protein assay should be avoided.

IV. Placing the Protein on the Plate

A. The protein can be added to a multiwell plate using the same procedures described in Section II.

B. Solvent Removal

Solvents used to aid in addition of the protein to the multiwell plates can be removed by essentially the same procedures described in Section IF, but care must be taken to ensure that the dye response is not decreased by protein hydrolysis during drying. If necessary, this can be prevented by removing the solvent by evaporation of the frozen solution (lyophilization), or by using nonaqueous solutions, or by incorporating a "stabilizer" layer between the protein solution and the assay components (see Section V).

V. Use of Prepared Standards

The solventless combined protein standards and assay reagents in the wells of a multiwell plate should be dissolved by adding an appropriate solvent, similar to that of the solution to be assayed, but without protein. Upon addition of the solvent, a reaction occurs between the solventless protein and dye within the well. Furthermore, the protein concentration of a solution can be determined by applying the protein-containing solution to a neighboring well containing only the solventless assay dye. The unknown protein concentration of the solution can be then determined by comparing the dye response in each of the wells containing known concentrations of protein with the response in the well containing the solution of unknown protein concentration.

It is critically important that the same volume of solvent is added to each of the wells in order to obtain an accurate estimation of the protein concentration of the unknown solution.

Thorough mixing of the solventless components with the aqueous solutions can be achieved by inverting the (re-sealed) multiwell plate or by agitating the plate. Mixing by agitation is most conveniently performed by using a plate reader with this capacity, but a vortex mixer, shaker, or sonicator may also be used.

Normally, upon addition of solvent to a well containing the solventless reagents, the dye will react with any protein present in the solvent, and, in those wells used to determine the standard curve, with the previously anhydrous protein already present in the well. In some cases, however, the solvent may contain substances which interfere with the protein-dye reaction. If the interference is uniform, and small relative to the response from the protein-dye reactions of the protein standards, it can be measured and eliminated by subtracting it from the dye response of each sample. An example of this type of interference would be a small dye response due to traces of protein or detergents from the inadequately rinsed glassware. If the interference is large, however, it presents a more serious problem. For example, proteins or detergents are sometimes added to solutions to stabilize or protect a particular enzyme or protein of interest In such cases, the added protein or detergent may cause such a large dye reaction that it is impossible to determine the concentration of the other proteins in the solution. With the assay procedures described, serious interference will cause all the wells in the column of protein standards to show the same dye response (usually the maximum absorbance change) rather than the normal, protein concentration-depended response gradient. This effect can be immediately detected by visual inspection, alerting the user to the problem. Often such interference can be prevented or minimized in subsequent assays by pre-diluting the solutions to allow a normal, protein-based dye response.

Other acidic media are also possible (see Table 2). The necessary features are the ability to maintain a pH of 1.1, low volatility, solid or semi-solid dry form, compatibility with the other components of the assay and the plastic multiwell plate, and long term stability.

TABLE 2

Acids Compatible with the Improved Assay*

Sodium bisulfate ($NaHSO_4$);

Potassium bisulfate ($KHSO_4$);

Tetramethylammonium hydrogen sulfate (($CH_3)4NHSO_4$);

Benzene-carboxylic acid;

Benzene-pentacarboxylic acid;

Benzene-hexacarboxylic acid;

Organic phosphoric acids such as

Glucose-1-phosphoric acid;

Oxalic acid;

Benzene sulfonic acids such as Benzene sulfonic acid or Benzene disulfonic acid.

*Mixtures of some or all of these acids, or mixtures of some or all of these acids with combined with sulfuric acid ($H_2SO_4$), phosphoric acid ($H_3PO_4$), or both, would also be compatible with the improved assay.

TABLE 3
Compounds Acting as Stabilizers in the Improved Assay

Diethylene glycol;

2-(2-methoxyethoxy) ethanol;

Diethylene glycol monobutyl ether;

Triethylene glycol;

triethylene glycol monomethyl ether;

Tetraethylene glycol;

Polyethylene glycol having an average molecular weight of 400 (PEG 400);

Propylene glycol;

Dipropylene glycol

Dipropylene glycol monomethyl ether;

Triproylene glycol monomethyl ether

Polyethylene glycol 1000 (PEG 1000);

Glucose;

Glycerol;

Ethylene glycol.

Some of the advantages of the improved solventless protein assay of the present invention with particular reference to the Bradford-style assay are listed below.

1. The solventless assay media is more stable than the stock assay solutions used in the Bradford assay, and does not require filtering or mixing immediately prior to use.
2. The solid anhydrous dye reagents allow receptacles containing these reagents to be tipped or inverted without flow or loss of the dye reagents, and prevent mixing between the anhydrous dye reagents and anhydrous protein in the same receptacle and if protein standards are included with the assay reagents.
3. The added stabilizers act to stabilize the dye-protein response during the assay, and decrease the precipitation of the dye-protein complex formed upon solution addition, as well as protect anhydrous proteins from the anhydrous dye reagent.
4. The added stabilizers act to decrease the surface tension of the assay solution and thereby destabilize any bubbles inadvertently formed during mixing of the dye reagent and solution.
5. Solutions of protein assay standards having exactly the same nonprotein composition as the samples to be assayed are easily prepared, simply by using the same buffer.
6. Several protein determinations can be made at the same time, and relative protein concentrations can be determined visually.
7. Common assay errors due to interfering substances in the solutions are immediately obvious by their visible effect on the color changes of the protein standards. Similarly, high sample protein concentrations are quickly obvious, and more dilute samples can be prepared and assayed immediately.
8. Reproducibility is improved because the protein standards and sample assay conditions are more uniform from assay to assay.
9. Sample protein concentrations can be rapidly and easily quantified by visually matching the color of the sample to that of the closest protein standard. More exact quantification also can be made rapidly, using a multiwell plate reader.
10. Only one precise volumetric measurement is required for each standard and sample, the volume of solution added to the well. This volume, typically 100 $\mu$L, can be measured conveniently and accurately.
11. Additional samples may be assayed using the same protein standards, as long as they are in the same buffer and are applied soon after the standards.
12. Degradation of protein standards by hydrolysis, proteolysis, or bacterial or fungal contamination is prevented by the anhydrous storage conditions.
13. The unused, sealed plates or well strips can be stored at room temperature, and are more compact and easily stored than other assay components and standards.
14. The resealed plates are quite stable, and with re-mixing, can usually be analyzed several days after preparation with little loss in sensitivity or accuracy.
15. The measurable protein concentration range, over 3 orders of magnitude, is greater than the standard Bradford assay.
16. The sensitivity is increased because the sample is not diluted in assay buffer.

EXAMPLE 1

Composition and Preparation of the Improved Protein Assay

Dye solution was prepared by dissolving 50 mg of purified Coomassie Blue G250 (C.I. #42655) in 25 mL of methanol. The acidic component of the dye reagent solution was prepared from commercial (Fisher) sodium bisulfate hydrate ($NaHSO_4 \cdot H_2O$) and sulfuric acid ($H_2SO_4$), and diluted in distilled and deionized water.

Protein assay receptacles were 96-well multiwell strip plates with 8-well strips (Nunc, Polysorp or Costar). Using an 8-channel syringe dispenser, 40 $\mu$L of an aqueous solution containing 1.6 M $H_2SO_4$ and 3.8 M $NaHSO_4$ was added to each well, followed by 10 $\mu$L of a solution containing 2 mg/mL Coomassie Blue G250 in methanol. Upon adding the Coomassie Blue G250 solution to a well, the well contents were initially blue. The solution then slowly turns red and a white precipitate forms. The precipitate then dissolves. This series of events reflects the acidification of the Coomassie Blue G 250 followed by the methanol-induced $NaHSO_4$ precipitation. As the methanol evaporates, the $NaHSO_4$ again dissolves. After addition of the dye, 10 $\mu$L of triethylene glycol was added. Alternatively, the stabilizer can be added after the solvents have been removed.

The multiwell plates containing the assay media and solvents were tipped at an angle of approximately 70° from horizontal, and the water and methanol were removed from the plates by evaporation. Moderate heat (50° C.) with a stream of dry air for approximately 12 hours, or under vacuum (12 torr partial pressure) at the same temperature for 5–6 hours was sufficient to remove the solvents. Drying was continued until no further weight loss was observed. The dry plates, with the anhydrous assay reagents forming a solid mass on one side of each receptacle, were transferred to a desiccator, sealed, and cooled to room temperature. After drying, each well contained 6.2 mg of $H_2SO_4$, 18.2 mg of $NaHSO_4$, 20 $\mu$g of Coomassie Blue G 250 and 10 $\mu$L of triethylene glycol, and had a total dried reagent volume of approximately 20 µL.

Bovine serum albumin (BSA) standard protein solutions were prepared by dissolving the appropriate amount of BSA in 0.09% saline to produce a 2 mg/mL BSA solution, which was diluted with saline to give a series of solutions with BSA concentrations of 0, 10, 20, 50, 100, 200, 500, 1000 µg/mL. To prevent contact between the protein standards and the assay reagents in the multiwell plates, the plates containing the anhydrous assay reagents were tipped at an angle of approximately 70° from horizontal to place the anhydrous assay reagents on the top side of each receptacle, and the BSA solutions, in 10 µL aliquots in order of increasing concentration, were carefully placed into the receptacles in rows A–H of several 8-well strips of the multiwell plates. While keeping the multiwell plates at a 70° angle, the water was removed from the plates by evaporation with a stream of dry air and moderate heat (50° C.) or under vacuum (partial pressure 12 torr) at room temperature until no further weight loss was observed. The dry plates, with the anhydrous assay reagents forming a solid mass on one side of each receptacle and the protein standards, when present, forming a layer on the other side of the receptacle, were sealed with multiwell sealing tape (Corning) or placed in zip-lock plastic bags and stored to room temperature.

For protein assays, a standard response curve relating the change in absorbance to protein concentration was generated using added protein standards or using wells containing dried protein standards. If dried protein standards were used, protein assays were performed by removing two strips (columns) of wells from a multiwell plate, one strip with both the dye reagents and protein standards, and one strip of assay wells containing only the dye reagents. If the wells were sealed with tape, the tape is peeled back from the strip of wells containing the dye reagents and protein standards and from the strip of assay wells containing only the dye reagents. An exact volume (100 µL) of the protein solution to be assayed was added to one or more wells of the assay strip, and the same volume of the same buffer solution, but without the protein to be assayed, was added to each well of the strip containing the protein standards. Sample volumes of 75 µL to 200 µL per well will give a good response, with the optimum response at 100 µL per well. Of course, the same volume must be added to each of the wells used for the protein standards and the wells used to assay the protein of unknown concentration. The wells were carefully resealed with the tape strip and the solutions mixed by shaking. The plate can be read immediately, but the protein-dependent dye response is quite stable, and shows only a modest decrease in absorbance on the following day. The tape strip either can be left in place or can be carefully peeled back before reading the strips, to avoid the higher background absorbance it causes. Using a multiwell plate reader, the absorbance can be read at wavelengths from 590 nm to 630 nm, with the absorbance maximum for the protein-dye complex at about 600 nm.

A similar procedure was used to make a simple visual protein determination, except the same volume (100 µL) of the protein sample solution was added to all the wells of an assay strip. By adding the sample solution to be assayed to all the wells in a strip, a simple side-by-side color comparison can be made between the wells in the standard column and the wells in the sample column.

EXAMPLE 2

A single solution containing all the components required for the assay was prepared as described below. Dye solution was prepared by dissolving 18 mg of Coomassie Blue G250 (C.I. #42655) in 15 mL of triethyene glycol. After the dye had dissolved, the solution was added to 45 mL of solution containing 4.4 M sodium bisulfate hydrate (NaHSO$_4$.H$_2$), 0.5 M sulfuric acid (H$_2$SO$_4$), and 32 mg/mL glucose. The resulting solution had a pH of 0.5 and was quite stable, showing no evidence of deterioration or precipitation'even after standing for several weeks at room temperature.

Protein assay receptacles were 96-well plates as described in the previous example. Using an 8-channel syringe dispenser, 40 µL of the combined acid-dye reagent was added to each well, and the plates dried as described in the previous example. After drying, each well contained 1.5 mg of H$_2$SO$_4$, 16 mg of NaHSO$_4$, 1 mg glucose, 12 µg of Coomassie Blue G250 and 10 µL of triethylene glycol. The total dried reagent volume was approximately 16 µL/well. Protein assays were performed as described in the previous example.

What is claimed is:

1. A method for preparing a solventless dye assay reagent comprising:

preparing a dye reagent solution containing a brilliant blue dye Color Index (C.I.) 42655, a dye solvent and a sodium bisulfate;

placing an aliquot of the dye reagent solution within a receptacle;

removing the dye solvent under conditions wherein the sodium bisulfate precipitates, crystallizes or solidifies.

2. The method of claim 1 wherein a stabilizer is added to the dye reagent solution.

3. The method of claim 2 wherein the stabilizer is selected from the group consisting of diethylene glycol, 2-(2-methoxyethoxy) ethanol, diethylene glycol monobutyl ether, triethylene glycol, triethylene glycol monomethyl ether, tetraethylene glycol, polyethylene glycol 400, propylene glycol, dipropylene glycol, dipropylene glycol monomethyl ether, triproylene glycol monomethyl ether, polyethylene glycol 1000, glucose; glycerol and ethylene glycol.

4. A solventless dye reagent produced according to the process of claim 1.

5. The solventless dye reagent of claim 4 further comprising a stabilizer.

6. The solventless dye reagent of claim 5 wherein the stabilizer is selected from the group consisting of diethylene glycol, 2-(2-methoxyethoxy) ethanol, diethylene glycol monobutyl ether, triethylene glycol, triethylene glycol monomethyl ether, tetraethylene glycol, polyethylene glycol 400, propylene glycol, dipropylene glycol, dipropylene glycol monomethyl ether, triproylene glycol monomethyl ether, polyethylene glycol 1000, glucose; glycerol and ethylene glycol.

7. A method for preparing a solventless protein standard comprising the steps of:

preparing a dye reagent solution containing a brilliant blue dye, Color Index 42655, a dye solvent and sodium bisulfate;

placing an aliquot of the dye reagent solution within a receptacle;

removing the dye solvent under conditions wherein the sodium bisulfate precipitates;

preparing a protein solution containing a known amount of protein and a known amount of protein solvent;

placing a known amount of the protein solution within the receptacle containing the dye such that the amount of protein within the receptacle can be calculated; and removing the protein solvent.

8. A protein assay standard produced according to the process of claim 7.

9. The method of claim 7 further comprising; placing an aliquot of the dye reagent solution into a number of wells of a multiwell plate and removing the dye solvent in each well under conditions wherein the sodium bisulfate precipitates;

preparing a number of separate protein solutions, each protein solution having a different known amount of protein and a known amount of protein solvent, wherein the concentration of protein within each protein solution is known and is different than the concentration of the other solutions;

placing a known amount of each of the protein solutions into separate dye reagent containing wells of the multiwell plate; and removing the protein solvent from wells containing a protein solution.

10. A multiwell plate containing a protein assay standard produced according to the process of claim 9.

11. A method for preparing a solventless protein standard comprising the steps of:

preparing a protein solution containing a known amount of protein and a known amount of protein solvent;

placing a known amount of the protein solution within a receptacle such that the amount of protein within the receptacle can be calculated;

removing the protein solvent;

preparing a dye reagent solution containing a brilliant blue dye, Color Index 42655, dye solvent and sodium bisulfate;

placing an aliquot of the dye reagent solution within the receptacle containing the protein solution; and removing the dye solvent under conditions wherein the sodium bisulfate precipitates.

12. A protein assay standard produced according to the process of claim 11.

13. A method for determining the concentration of total protein in a solution comprising:

preparing a dye reagent solution containing a brilliant blue dye, Color Index 42655, a dye solvent and sodium bisulfate;

placing an aliquot of the dye reagent solution into each of a series of wells within a multiwell plate;

removing the dye solvent under conditions wherein the sodium bisulfate precipitates;

preparing a number of separate protein solutions, each protein solution containing a different known amount of protein and a known amount of protein solvent, wherein the concentration of protein within each protein solution is known and is different than the concentration of the other solutions;

placing a known amount of each of the protein solutions into separate dye reagent containing wells such that the amount of protein within each well is different;

removing the protein solvent from the protein containing wells;

adding a predetermined uniform volume of solvent to each of the wells which contain protein so as to produce a detectable visual protein-dye reaction wherein the visual protein-dye reaction in each of the wells has an intensity which corresponds to the concentration of protein within each of the wells;

adding a volume of a protein solution having an unknown concentration of protein to a well which only contains a solventless dye and no protein, the volume of unknown protein solution being in an amount equal to the volume of solvent added to the protein-dye containing wells, wherein the protein in the unknown solution reacts with the dye in the well to produce a detectable visual protein-dye reaction which has a measurable intensity; and comparing the intensity of the protein-dye reaction within the well containing the protein solution having an unknown concentration of protein with the intensities of the protein-dye reactions of the wells containing known amounts of protein so as to determine the concentration of protein within the unknown protein solution.

14. The method of claim 13 further comprising adding a stabilizer to the dye solution.

15. The method of claim 14 wherein the stabilizer is selected from the group consisting of diethylene glycol, 2-(2-methoxyethoxy) ethanol, diethylene glycol monobutyl ether, triethylene glycol, triethylene glycol monomethyl ether, tetraethylene glycol, polyethylene glycol 400, propylene glycol, dipropylene glycol, dipropylene glycol monomethyl ether, triproylene glycol monomethyl ether, polyethylene glycol 1000, glucose; glycerol and ethylene glycol.

16. A method for determining the concentration of total protein in a solution comprising:

preparing a number of separate protein solutions, each protein solution containing a different known amount of protein and a known amount of protein solvent, wherein the concentration of protein within each protein solution is known and is different than the concentration of the other solutions;

preparing a dye reagent solution comprised of a brilliant blue dye, Color Index 42655, a dye solvent and sodium bisulfate;

placing a known amount of each of the protein solutions into separate wells of a multiwell plate such that the amount of protein within each well is different;

removing the protein solvent from the protein containing wells;

placing an aliquot of the dye reagent solution into each of the wells containing solventless protein and an aliquot of the dye reagent solution into at least one well which does not contain solventless protein;

removing the dye solvent under conditions wherein the sodium bisulfate precipitates;

adding a predetermined uniform volume of solvent to each of the wells which contain protein so as to produce a detectable visual protein-dye reaction wherein the visual protein-dye reaction in each of the wells has an intensity which corresponds to the concentration of protein within each of the wells;

adding a volume of a protein solution having an unknown concentration of protein to a well which only contains a solventless dye and no protein, the volume of unknown protein solution being in an amount equal to the volume of solvent added to the protein-dye containing wells, wherein the protein in the unknown solution reacts with the dye in the well to produce a detectable visual protein-dye reaction which has a measurable intensity; and comparing the intensity of the protein-dye reaction within the well containing the protein solution having an unknown concentration of protein with the intensities of the protein-dye reactions of the wells containing known amounts of protein so as to determine the concentration of protein within the unknown protein solution.

17. The method of claim 16 further comprising adding a stabilizer to the dye solution.

18. The method of claim 7 wherein the stabilizer is selected from the group consisting of diethylene glycol, 2-(2-methoxyethoxy) ethanol, diethylene glycol monobutyl ether, triethylene glycol, triethylene glycol monomethyl ether, tetraethylene glycol, polyethylene glycol 400, propylene glycol, dipropylene glycol, dipropylene glycol monomethyl ether, triproylene glycol monomethyl ether, polyethylene glycol 1000, glucose; glycerol and ethylene glycol.

* * * * *